US006431001B1

(12) United States Patent
Tsuzuki et al.

(10) Patent No.: US 6,431,001 B1

(45) Date of Patent: Aug. 13, 2002

(54) OBSTACLE DETECTING SYSTEM HAVING SNOW DETECTING FUNCTION

(75) Inventors: Takeo Tsuzuki, Toyota; Takanobu Sasaki, Anjo; Kenichi Ohue; Tomoyuki Funayama, both of Toyota, all of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/918,529

(22) Filed: Aug. 1, 2001

(30) Foreign Application Priority Data

Aug. 31, 2000 (JP) ....................................... 2000-263797

(51) Int. Cl.[7] ........................... G01N 25/00; B60Q 1/00

(52) U.S. Cl. ............................. 73/617; 73/586; 73/609; 73/436

(58) Field of Search .......................... 73/617, 609, 579, 73/597, 598, 602, 627, 629, 1.48, 586; 340/436, 581, 435

(56) References Cited

U.S. PATENT DOCUMENTS 3,781,566 A * 12/1973 Meuller ...................... 307/116
5,345,223 A * 9/1994 Rutkiewicz ................. 340/581
5,574,426 A * 11/1996 Shisgal et al. .............. 340/435
5,844,471 A * 12/1998 Daniel ........................ 340/436
6,127,964 A * 10/2000 Kageyama ................... 342/70

FOREIGN PATENT DOCUMENTS

| | | | | | |
|---|---|---|---|---|---|
| JP | A-61-83978 | | 4/1986 | | |
| JP | A-63-33684 | | 2/1988 | | |
| JP | 401029791 A | * | 1/1989 | .................. | 73/596 |
| JP | A-3-108682 | | 5/1991 | | |
| JP | A-4-242189 | | 8/1992 | | |
| JP | 363154979 A | * | 6/1998 | .................. | 342/26 |

* cited by examiner

*Primary Examiner*—Hezron Williams
*Assistant Examiner*—Jacques Saint-Surin
(74) *Attorney, Agent, or Firm*—Law Offices of David G. Posz

(57) ABSTRACT

An obstacle detecting system for vehicles has an ultrasonic vibrator having a vibration plate and mounted on a vehicle to transmit and receive an ultrasonic wave. An obstacle is detected in response to an output signal of the ultrasonic vibrator. When the temperature around the ultrasonic vibrator is below a predetermined temperature corresponding to snowfall, the system calculates a ratio of a period of reverberating vibration of the ultrasonic vibrator relative to a predetermined time period following an ultrasonic wave transmission, and determines accumulation of snow when the calculated ratio exceeds a predetermined time ratio. The system notifies an abnormality of the ultrasonic vibrator arising from the accumulation of snow.

8 Claims, 3 Drawing Sheets

20
DRIVER
10
12
UV
11
30
BPF
40
AMPLI-
FIER
50
ENVELOPE
DETECTOR
70
MICRO-
COMPUTER
TEMPERATURE
SENSOR
60
90
DRIVER
80
DISPLAY
DRIVER
110
BUZZER
100

OBSTACLE DETECTING SYSTEM HAVING SNOW DETECTING FUNCTION

CROSS REFERENCE TO RELATED APPLICATION

This application is based on and incorporates herein by reference Japanese Patent Application No. 2000-263797 filed Aug. 31, 2000.

BACKGROUND OF THE INVENTION

The present invention relates to an obstacle detecting system, which detects obstacles against a vehicle by the use of an ultrasonic wave.

Obstacle detecting systems for vehicles use an ultrasonic vibrator, which transmits an ultrasonic wave and receives the ultrasonic wave reflected by an obstacle. The ultrasonic vibrator has a casing, a piezoelectric device provided in the casing, and a vibration plate made of an aluminum film and provided in the opening of the casing.

The piezoelectric vibrator vibrates at a frequency of the drive voltage applied thereto. The vibration of the piezoelectric vibrator is transmitted to the vibration plate, so that the casing resonates with the vibration. Thus an ultrasonic wave is transmitted from the vibration plate. The casing continues to resonate by inertia vibration after the piezoelectric device stops the vibration, resulting in reverberating vibration. Thus, the ultrasonic vibrator transmits the ultrasonic wave in response to the vibration of the piezoelectric device and the reverberating vibration.

The ultrasonic vibrator is mounted on a vehicle in such a manner that the vibration plate is exposed to the exterior of the vehicle. As a result, snow tends to stick to or accumulate on the vibration plate of the ultrasonic vibrator in winter, thereby increasing the weight of the vibration plate. The casing therefore continues the reverberating vibration for a longer period at a frequency, which is slightly deviated from its resonant frequency.

Under this condition, the ultrasonic vibrator is likely to continue to transmit the ultrasonic wave even after starting to receive a reflected ultrasonic wave. It is difficult to distinguish whether the output signal of the ultrasonic vibrator results from the reflected wave or the reverberating vibration. Thus, the obstacle detection system tends to detect that an obstacle exists close to the vehicle although it exists remote from the vehicle.

SUMMARY OF THE INVENTION

It is an object of the present invention to provide an obstacle detecting system, which is capable of detecting and notifying accumulation of snow on an ultrasonic vibrator.

According to the present invention, an obstacle detecting system for vehicles comprises an ultrasonic vibrator having a vibration plate and mounted on a vehicle to transmit and receive an ultrasonic wave, and an obstacle is detected in response to an output signal of the ultrasonic vibrator. The system checks whether the vibration plate has accumulation of snow based on a period of reverberating vibration of the vibration plate, and notifies an abnormality of the ultrasonic vibrator arising from the accumulation of snow.

Preferably, the system executes a snow accumulation check operation only when the temperature around the ultrasonic vibrator is below a predetermined temperature corresponding to snowfall. The system calculates a ratio of the period of reverberating vibration of the ultrasonic vibrator relative to a predetermined time period following an ultrasonic wave transmission, and determines the accumulation of snow when the calculated ratio exceeds a predetermined time ratio.

BRIEF DESCRIPTION OF THE DRAWINGS

The above and other objects of the present invention will become more apparent from the following detailed description made with reference to the accompanying drawings. In the drawings.

DETAILED DESCRIPTION OF THE PREFERRED EMBODIMENT

Figure 1:
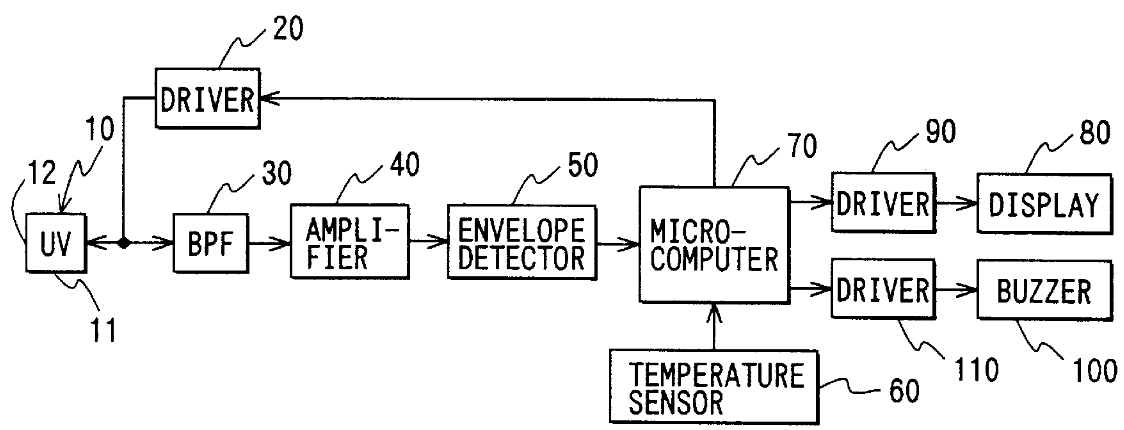
FIG. 1 is a block diagram showing an obstacle detecting system according to an embodiment of the present invention.

Referring to FIG. 1, an obstacle detecting system is constructed as a rear sonar for a vehicle. It has an ultrasonic vibrator 10. This ultrasonic vibrator 10 is mounted on a rear bumper of the vehicle at a central position in the right-left direction of the vehicle for detecting any obstacle existing in the rear direction of the vehicle. This ultrasonic vibrator 10 comprises a casing 11, a vibration plate 12 attached to the casing 11 for transmitting and receiving ultrasonic waves, and a piezoelectric device (not shown) provided in the casing 11 for vibrating the vibration plate 12. The vibration plate 12 is exposed to the rear outside of the vehicle so that the ultrasonic waves are radiated in the rearward direction.

In the ultrasonic vibrator 10 the piezoelectric device vibrates when driven with a driving voltage. This vibration is transmitted to the vibration plate 12 to vibrate the vibration plate 12. The ultrasonic vibrator 10 transmits ultrasonic waves outward (rearward of the vehicle) by the vibration of the vibration plate 12. The ultrasonic vibrator 10 receives at the vibration plate 12 ultrasonic waves reflected by obstacles, and vibrates at a frequency of the reflected wave. The vibration plate 12 transmits this vibration to the piezoelectric device, which in turn generates a piezoelectric voltage as a reception signal. This reception signal has a magnitude proportional to the received reflected wave.

The drive voltage for the piezoelectric device is set to 40 kHz so that the ultrasonic wave is transmitted at this frequency. The casing 11 is constructed to resonate at this frequency. As a result, the casing 11 starts to resonate when the vibration of the piezoelectric device is transmitted to the vibration plate 12. The casing 11 continues to resonate by inertia, as reverberating vibration, even after the transmission of vibration of the piezoelectric device stops.

The obstacle detecting system also has a driver circuit 20, a band pass filter circuit (BPF) 30, an amplifier circuit 40, an envelope detector circuit 50, a temperature sensor 60, a microcomputer 70, a display 80, a buzzer 100, and driver circuits 90 and 110.

The driver circuit 20 is controlled by the microcomputer 70 to generate oscillation pulse signal at a frequency of 40 kHz to drive the piezoelectric device of the ultrasonic vibrator 10. Specifically, the driver circuit 20 generates the oscillation pulse signal, which lasts 250 $\mu$s each time 150 ms elapses after the previous oscillation period (250 μs). This 150 ms is set as a transmission stop period.

The BPF 30 filters out noise signal from the reception signal produced from the ultrasonic vibrator 10 to produce a filter signal. The amplifier circuit 40 amplifies the filter signal (FIGS. 3 and 4) to produce an amplified signal. The envelope detector circuit 50 detects an envelope of the amplified signal. The temperature sensor 60 detects temperature around the ultrasonic vibrator 10.

Figure 2:
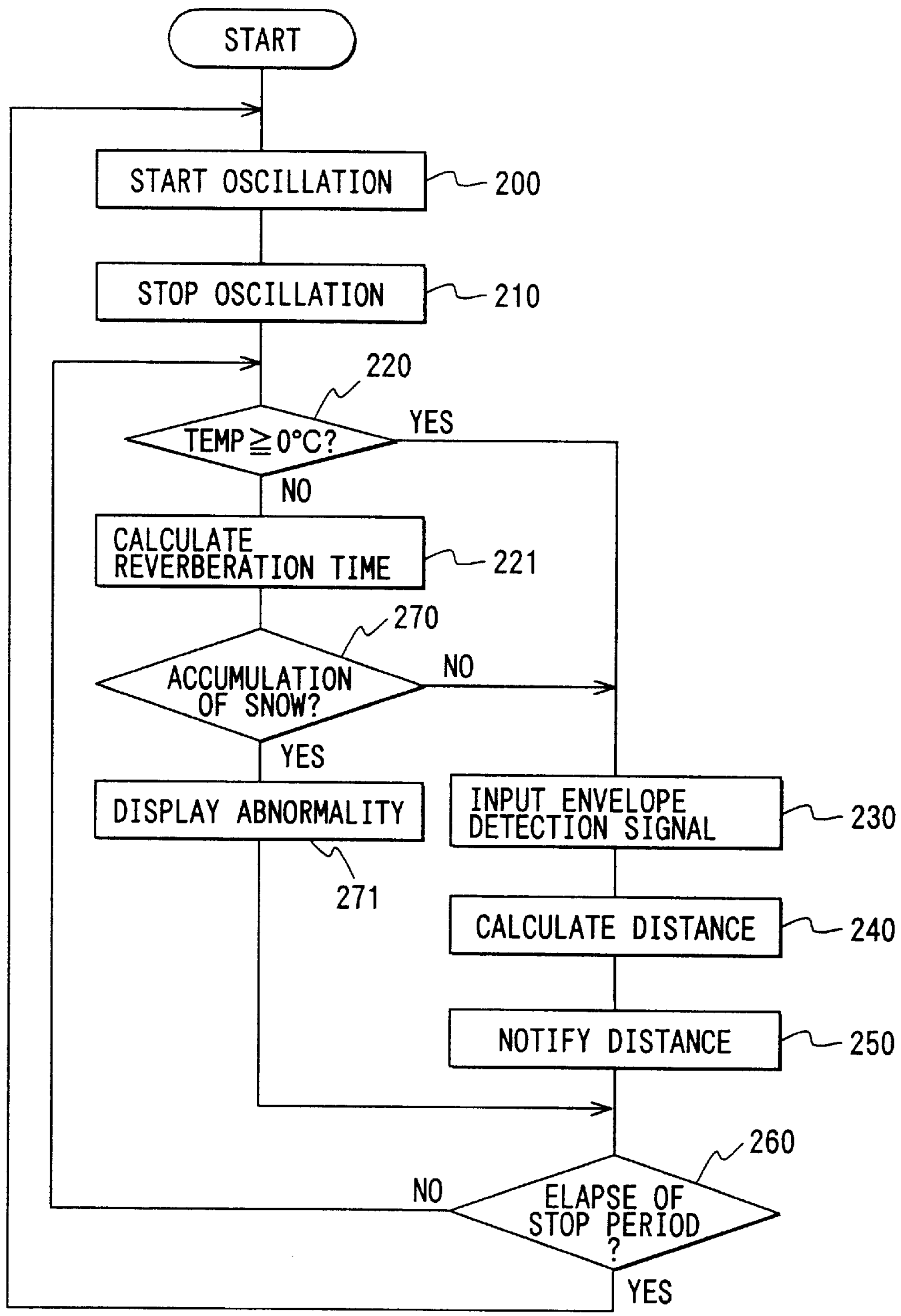
FIG. 2 is a flow diagram showing a control process of a microcomputer used in the embodiment shown in FIG. 1.

The microcomputer 70 is programmed to execute a control process shown in FIG. 2 to calculate a distance of the vehicle to an obstacle in response to the envelop-detected signal. The display 80 and the buzzer 100 are mounted on an instrument panel of the vehicle. The display 80 and the buzzer 100, driven by the driver circuits 90 and 110, respectively notify visually and audibly the calculated distance and existence of the obstacle.

Operation of the obstacle detecting system, particularly operation of the microcomputer 70, is described with reference to FIG. 2. The microcomputer 70 causes the driver circuit 20 to generate the oscillation pulse signal at 40 kHz at step 200. The piezoelectric device of the ultrasonic vibrator 10 is driven with this drive voltage to transmit the ultrasonic wave from the vibration plate 12. The microcomputer 70 stops generation of the oscillation pulse signal of the driver circuit 20 at step 210 after the oscillation period of 250 μs. Thus, the vibration of the piezoelectric device stops. When the piezoelectric device stops vibration, the ultrasonic vibrator is switched from the transmission mode to the reception mode.

The microcomputer 70 checks at step 220 whether the temperature of the ultrasonic vibrator 10 detected by the temperature sensor 60 is equal to or higher than 0° C. If the check result is YES indicating no sticking nor accumulation of snow, the microcomputer 70 inputs the envelope detection signal from the envelope detector 50. This envelope detection signal corresponds to the ultrasonic wave reflected by the obstacle and received by the ultrasonic vibrator 10.

Figure 3:
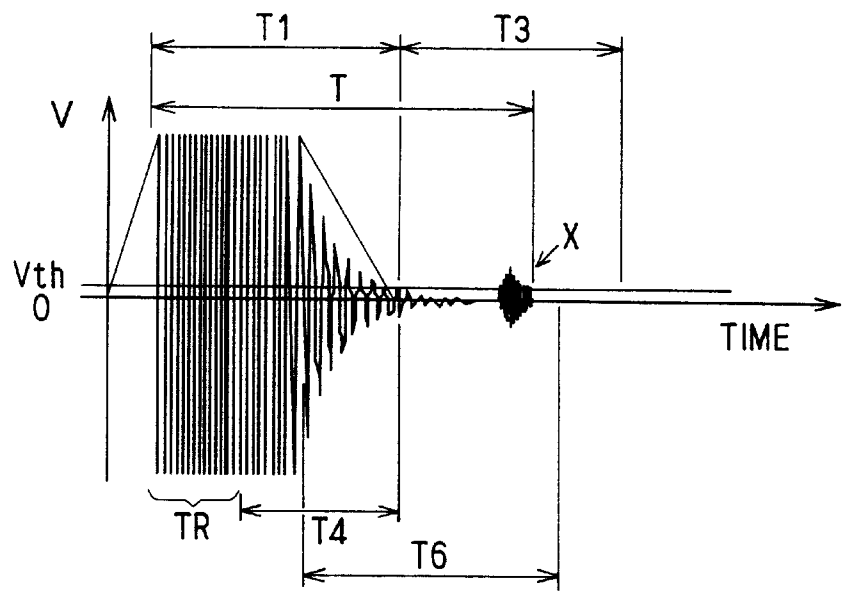
FIG. 3 is a signal diagram showing an output of an amplifier used in the embodiment when an ultrasonic vibrator has no accumulation of snow.
Figure 4:
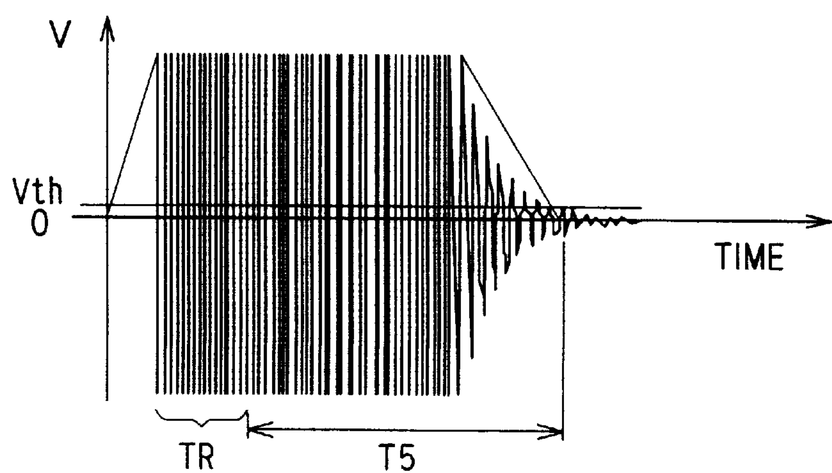
FIG. 4 is a signal diagram showing an output of the amplifier when the ultrasonic vibrator has accumulation of snow.

The microcomputer 70 calculates a distance between the vehicle and an obstacle at step 240 by using the amplified signal or the envelope detection signal. Specifically, the distance is calculated as follows. The amplified signals are shown in FIGS. 3 and 4 in case of no snow accumulation and snow accumulation, respectively. First, a time period T in which the amplitude of the ultrasonic wave X, that is, the amplitude V of the amplified signal, exceeds a threshold Vth as shown in FIG. 3, is measured in a predetermined period T3 (1.4 ms) following a predetermined period T1 (1.6 ms) from the start of transmission of the ultrasonic wave of the ultrasonic vibrator 10. The distance is calculated as a product of the propagation speed of the ultrasonic wave and one half of the measured time period T. The predetermined period T1 is set to correspond to a period from the start of ultrasonic wave transmission to the end of reverberation in the normal (no snow) condition, thus covering a transmission period TR (oscillation pulse generation period 0.25 ms) and a reverberation period T4.

The microcomputer 70 causes at step 250 the driver circuit 90 to drive the display 80 so that the calculated distance is displayed visually. At the same time, the microcomputer 70 causes the driver circuit 110 to drive the buzzer if the calculated distance is less than a predetermined distance.

If the check result at step 220 is NO indicating snow, the microcomputer 70 calculates, as the reverberating period, the time period T4 or T5, in which the magnitude V of the amplified signal exceeds the threshold Vth after the transmission of the ultrasonic wave.

The microcomputer 70 checks at step 270 whether the ultrasonic vibrator 10 has an accumulation of snow thereon. The microcomputer 70 determines accumulation of snow if the calculated period of reverberating vibration is more than 70% of a predetermined time period T6 (2.5 ms), which is after 1.2 ms from the start of ultrasonic wave transmission.

If no snow accumulates on the ultrasonic vibrator 10, the reverberating vibration continues for the period T4 as shown in FIG. 3. However if snow accumulates on the ultrasonic vibrator 10, the reverberating vibration continues for the period T5 as shown in FIG. 4. The period T5 is longer than the period T4. It was confirmed in the experiments that accumulation of snow can be detected by checking whether the time period T4 or T5 is in excess of a predetermined ratio (70%) of the predetermined time period T6 under the condition that the detected temperature is 0° C.

If the check result at step 270 is NO indicating no snow accumulation, the microcomputer 70 executes steps 230–250. If the check result is YES indicating snow accumulation, the microcomputer 70 causes at step 271 the driver circuit 90 to drive the display 80 so that abnormality of the ultrasonic vibrator 10 may be displayed. With this display, a driver of the vehicle is enabled to recognize that the ultrasonic vibrator 10 and hence the obstacle detecting system cannot operate normally.

The microcomputer 70 then checks at step 260 whether the predetermined transmission stop period (150 ms) has elapsed. If this check result is NO indicating that the system is still in the transmission stop period, the microcomputer 70 repeats the above process from step 220. If the check result is YES indicating that the system is now not in the transmission stop period, the microcomputer 70 repeats the whole process from step 200.

The present invention should not be limited to the above embodiment, but may be implemented in various ways. For instance, the ultrasonic vibrator 10 may be driven at a different frequency other than 40 kHz. The snow accumulation on the ultrasonic vibrator 10 may be notified by other devices such as voice or light. The reference temperature 0° C. for checking snowfall may be set to other temperatures. The ultrasonic vibrator 10 may be mounted on other locations of a vehicle such as outer peripheral wall parts of a vehicle so that this system may be used as clearance sonar. The accumulation of snow may be detected by comparing the reverberation period with a predetermined reference period.

What is claimed is:

1. An obstacle detecting system for vehicles comprising:

an ultrasonic vibrator having a vibration plate and mounted on a vehicle to transmit and receive an ultrasonic wave;

driver means for driving the ultrasonic vibrator at a predetermined frequency for an ultrasonic wave transmission;

detection means for detecting an obstacle in response to an output signal of the ultrasonic vibrator;

snow check means for checking whether the vibration plate has snow thereon based on a period of reverberating vibration of the vibration plate; and notification means for notifying an abnormality of the ultrasonic vibrator arising from snow;

wherein the snow check means has a temperature sensor for detecting a temperature around the ultrasonic vibrator, and executes a snow check operation only when the detected temperature is below a predetermined temperature corresponding to snowfall.

2. The obstacle detecting system as in claim 1, wherein: the snow check means calculates a ratio of the period of reverberating vibration of the ultrasonic vibrator relative to a predetermined time period following an ultrasonic wave transmission, and determines accumulation of snow when the calculated ratio exceeds a predetermined time ratio.

3. The obstacle detecting system as in claim 1, wherein: the ultrasonic vibrator has a casing attached to the vehicle and having an opening in which the vibration plate is provided, and a piezoelectric device provided in the casing and driven by the driver means to vibrate the casing and the vibration plate.

4. The obstacle detecting system as in claim 1, wherein: the notifying means has a display and a buzzer for notifying the abnormality of the ultrasonic vibrator.

5. The obstacle detecting system as in claim 1, wherein the snow check means checks whether the vibration plate has snow thereon by comparing the period of reverberating vibration of the vibration plate with a predetermined reference period.

6. An obstacle detecting system for vehicles comprising:

an ultrasonic vibrator having a vibration plate and mounted on a vehicle to transmit and receive an ultrasonic wave;

driver means for driving the ultrasonic vibrator at a predetermined frequency for an ultrasonic wave transmission;

detection means for detecting an obstacle in response to an output signal of the ultrasonic vibrator;

snow check means for checking whether the vibration plate has snow thereon based on a period of reverberating vibration of the vibration plate; and notification means for notifying an abnormality of the ultrasonic vibrator arising from snow;

wherein the snow check means calculates a ratio of the period of reverberating vibration of the ultrasonic vibrator relative to a predetermined time period following an ultrasonic wave transmission, and determines accumulation of snow when the calculated ratio exceeds a predetermined time ratio.

7. An ultrasonic detecting system for vehicles comprising:

an ultrasonic vibrator having a vibration plate and mounted on a vehicle to transmit and receive an ultrasonic wave;

measuring means for measuring a time period of reverberating vibration of the vibration plate which follows a transmission of the ultrasonic wave;

detecting means for detecting a surrounding condition of the vehicle from the received ultrasonic wave only when the measured time period is in a normal range; and temperature detecting means for detecting a temperature around the ultrasonic vibrator, wherein the measuring means measures the time period of reverberating vibration only when the detected temperature is below a predetermined temperature.

8. The ultrasonic detecting system as in claim 7, wherein: the predetermined temperature is set to about 0° C. and the normal range is set to indicate no snow condition.

* * * * *